United States Patent [19]

Leibowitz et al.

[11] 4,364,863

[45] Dec. 21, 1982

[54] EXTRACTION OF INTERFERON FROM BACTERIA

[75] Inventors: Paul Leibowitz, Hackensack; Marvin J. Weinstein, East Brunswick, both of N.J.

[73] Assignee: Schering Corporation, Kenilworth, N.J.

[21] Appl. No.: 345,118

[22] Filed: Feb. 2, 1982

Related U.S. Application Data

[63] Continuation of Ser. No. 221,135, Dec. 29, 1980, Pat. No. 4,315,852, which is a continuation-in-part of Ser. No. 210,426, Nov. 16, 1980, abandoned.

[51] Int. Cl.$^3$ ............................................. A61K 45/02
[52] U.S. Cl. .................................. 260/112 R; 424/85; 424/87
[58] Field of Search ........................... 260/112; 424/85

[56] References Cited

U.S. PATENT DOCUMENTS

| 3,256,152 | 6/1966 | Lampson | 424/85 X |
|---|---|---|---|
| 3,265,581 | 9/1966 | Fantes et al. | 424/85 |
| 3,414,651 | 12/1968 | Fantes | 424/85 |
| 3,699,222 | 10/1972 | Isaacs et al. | 424/85 |
| 4,266,024 | 5/1981 | Swetly et al. | 424/85 X |
| 4,273,703 | 6/1981 | Osther et al. | 424/85 X |
| 4,276,282 | 6/1981 | Sugimoto et al. | 424/85 |
| 4,289,689 | 9/1981 | Friesen et al. | 424/85 X |

FOREIGN PATENT DOCUMENTS 2037296 9/1980 United Kingdom .

OTHER PUBLICATIONS

Nature, vol. 287, 193–197, (1980), Derynck et al.
Nature, vol. 284, 316–320, (1980), Nagata et al.
Science, vol. 209, 1343–1347, Streuli et al.

*Primary Examiner*—Howard E. Schain
*Attorney, Agent, or Firm*—Paul H. Ginsburg; Bruce M. Eisen

[57] ABSTRACT

A method of extracting leucocyte interferon from interferon-expressing bacterial cells comprising acidifying a suspension of interferon-containing bacterial cells, removing substantially all of the suspension liquid from the cells, preparing a second suspension of the acidified cells, neutralizing said second suspension, separating the interferon containing liquid from the suspended cells, and extracting the interferon from said liquid.

8 Claims, No Drawings

EXTRACTION OF INTERFERON FROM BACTERIA

This is a continuation of application Ser. No. 221,135, filed Dec. 29, 1980, now U.S. Pat. No. 4,315,852, which is, in turn, a continuation-in-part of U.S. Ser. No. 210,426, filed Nov. 26, 1980, now abandoned.

The present invention relates to extraction of interferon from interferon-expressing bacteria.

Although interferon is widely believed to be of great importance as a potential anti-viral and/or anti-cancer agent, the scarcity and great expense of interferon obtained from natural sources has delayed substantial clinical testing and widespread use of interferon. Recombinant DNA techniques have been used to create bacteria capable of expressing interferon. See, for example, Nagata et. al., Nature, vol. 284, 316–320 (1980), the disclosure of which is hereby incorporated herein by reference. Fermentation of such bacteria is expected to yield large quantities of interferon at substantially lower cost than would be possible utilizing natural sources of interferon. However, clinical use of interferon requires high purity material that is not contaminated by cell constituents or cell debris of the interferon-expressing bacteria. Contamination by such impurities could result in adverse reactions or in test results that are not reproducible. Accordingly, extraction of interferon from the cells of interferon-expressing bacteria in sufficiently high purity for clinical use presented a major problem.

We have suprisingly discovered that interferon may be extracted from interferon-expressing bacteria by the simple steps of acidifying a suspension of interferon-containing bacterial cells, removing and discarding substantially all of the suspension liquid from the cells, preparing a second suspension of the acidified cells, neutralizing said second suspension, separating the interferon-containing liquid from the suspended cells, and extracting the interferon from said liquid. By the method of the present invention, interferon is surprisingly released from the cells upon neutralization of the suspension of acidified cells, without the need for mechanical or enzymatic disruption of the cell surface. This method allows efficient recovery of interferon in a manner which significantly reduces contamination by cell constituents and make subsequent purification steps easier and less expensive.

In the method of the present invention, the suspension of interferon-expressing cells, which may be in a fermentation tank, is preferably acidified to a pH of about 1.3 to 4.0, more preferably to a pH of about 2.0 to 2.5. Examples of suitable acids that may be used in the acidification step are hydrochloric acid, nitric acid, surfuric acid and phosphoric acid. Hydrochloric acid, however, is not preferred because it may corrode the fermentation equipment used to culture the cells. Sulfuric acid and phosphoric acid are most preferred. Preferably, the aforementioned suspending media are aqueous.

The temperature range at which the bacterial cells are treated with acid should be from about ambient temperature (that is, not lower than about 15° C.) to about 40° C. If the temperature is too low, the bacteria will not be killed fast enough during the acid treatment. The maximum temperature is about 40° C. because degradation of the interferon may take place at higher temperatures.

After the cell suspension is acidified, the cells are removed from the liquid, preferably by centrifugation. If the cells are centrifuged to form a pellet they should be resuspended prior to neutralization. If the centrifuge is designed to use a portion of the suspending liquid to form a slurry of the centrifuged cells, there may be sufficient liquid in the slurry so that one can proceed to the neutralization step. The word "suspension" as used herein is intended to include such a slurry.

Preferably, the cell suspension is neutralized to a pH of about 7.0 to 8.0, preferably 7.2 to 7.6. Examples of suitable bases that may be used in the neutralization step are potassium hydroxide and sodium hydroxide.

Examples of bacteria that can be altered by recombinant DNA techniques to produce interferon and from which interferon may then be extracted using the method of the present invention are $E.$ $coli,$ $Bacillus$ $subtilis,$ actinomycetes and the like. The preferred bacteria are $E.$ $coli$ and $Bacillus$ $subtilis.$ $E.$ $coli$ are most preferred.

The method of the present invention may be used with bacteria that express leucocyte interferon. Such bacteria may be prepared by the method of Nagata et.al., Nature vol. 284, 316–320 (1980), the disclosure of which is hereby incorporated herein by reference. The method of the present invention may also be used with bacteria that express fibroblast interferon. Such bacteria may be prepared by the method of Derynck et.al., Nature, vol. 287, 193–197 (1980), the disclosure of which is hereby incorporated herein by reference. The method of the present invention is especially useful with bacteria that express human leucocyte interferon.

Leucocyte and fibroblast interferons have also been referred to by the nomenclature IFN-alpha and IFN-beta respectively. Each of the aforementioned types of interferons may also have different forms. See, for example, U.K. patent application Ser. No. GB 2 037 296 A, published July 9, 1980, the disclosure of which is hereby incorporated herein by reference, and Streuli et.al., Science, vol. 209, 1343–1347 (1980), the disclosure of which is hereby incorporated herein by reference.

The following example illustrates the method of the present invention, but is not intended to be limiting:

EXAMPLE

Add 100 ml of an innoculum of interferon-expressing HB-101 $E.$ $coli$ containing the plasmid Z-pBR322(Pst)/HcIF-SN35, prepared by the method of Nagata et.al., Nature, vol. 284, 316–320 (1980), to 9.9 liters of broth in 14 liter fermentor at 37° C. The broth is prepared from 330 g cerelose, 310 g yeast extract, 50 g $KH_2PO_4$, 10 g $MgSO_4 \cdot 7H_2O$ and water to make 9.9 liters.

Maintain the pH at 7.0 and maintain the temperature at 37° C. while aerating and agitating the mixture until the culture's growth reaches late exponential (5 to 7 hours). Then add 10 N phosphoric acid to the $E.$ $coli$ suspension in the fermentor until the pH of 2.1 is obtained and allow the mixture to stand for one hour while maintaining the temperature at 25° to 37° C. Periodically, recheck the pH of the mixture and, if necessary, readjust it to a pH of 2.1. The contents of the fermentor are then harvested and centrifuged at about 5000xg or above. After centrifugation, harvest the bacterial pellet. Resuspend the pellet as an approximately 10% weight/volume suspension of bacteria in an aqueous solution that is 50 mM Tris and 0.15 M NaCl (pH7.5) and add 3

N sodium hydroxide until a pH of about 7.3 is obtained (if the centrifuge that is available produces a slurry rather than a pellet, it may not be necessary to resuspend the product in the aforementioned aqueous solution and one may proceed to add 3 N sodium hydroxide to the slurry). Mix the resulting susspension for one hour at 4° C. and then centrifuge at 5000xg or above. Discard the pellet. The supernatant contains extracted α1 interferon (IFN-α1), as defined by Streuli et.al., Science, vol. 209, 1343–1347 (1980), Similarly, using a plasmid expressing α2 interferon, as defined by Streuli et.al., Science, vol. 209, 1343–1347 (1980), extract such interferon from a broth.

Similarly, using a plasmid expressing another type of leucocyte interferon (for example, an interferon selected from the interferons defined in U.K. patent application Ser. No. 2 037 296 A, published July 9, 1980) extract such interferon from a broth.

Similarly, using a plasmid expressing fibroblast interferon, extract such interferon from a broth.

Derivatives of the aforementioned plasmid Z-pBR 322 (Pst)/HcIF-SN-35 that express IFN-α1 more efficiently may be prepared. The method of the present invention is likewise applicable to extraction of interferon from bacteria containing such plasmids.

We claim:

1. A method of extracting fibroblast interferon from interferon-expressing bacterial cells comprising acidifying a suspension of interferon-containing bacterial cells, removing substantially all of the suspension liquid from the cells, preparing a second suspension of the acidified cells, neutralizing said second suspension, separating the interferon containing liquid from the suspended cells, and extracting the interferon from said liquid.

2. A method according to claim 1, wherein said suspension is acidified with sulfuric acid or phosphoric acid.

3. A method according to claim 1, wherein said suspension is acidified to a pH of about 1.3 to 4.0.

4. A method according to claim 1, wherein said suspension is acidified to a pH of about 2.0 to 2.5.

5. A method according to claim 1, wherein said second suspension is neutralized with potassium hydroxide or sodium hydroxide.

6. A method according to claim 1, wherein said second suspension is neutralized to a pH of about 7.0 to 8.0.

7. A method according to claim 1, wherein said second suspension is neutralized to a pH of about 7.2 to 7.6.

8. A method according to claim 1, wherein said bacteria is *E. coli.*

* * * * *